US00PP33232P3

(12) United States Plant Patent
Schoemaker

(10) Patent No.: US PP33,232 P3
(45) Date of Patent: Jul. 6, 2021

(54) ***HYDRANGEA* PLANT NAMED 'LC NO9'**

(50) Latin Name: *Hydrangea paniculata*
Varietal Denomination: LC NO9

(71) Applicant: Alex Frederick Schoemaker, Boskoop (NL)

(72) Inventor: Alex Frederick Schoemaker, Boskoop (NL)

(73) Assignee: Alex Schoemaker Living Creations Holding B.V., Boskoop (NL)

( * ) Notice: Subject to any disclaimer, the term of this patent is extended or adjusted under 35 U.S.C. 154(b) by 0 days.

(21) Appl. No.: 16/974,063

(22) Filed: Sep. 18, 2020

(65) Prior Publication Data

US 2021/0120717 P1 Apr. 22, 2021

Related U.S. Application Data

(60) Provisional application No. 62/973,658, filed on Oct. 17, 2019.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Hydrangea* plant named 'LC NO9', characterized by its upright to somewhat outwardly spreading plant habit; freely branching habit with strong lateral branches; early and freely flowering habit with plants remaining in flower for a long period time; dense and hardy inflorescences with large white-colored sterile and prominent white-colored fertile flowers; and good garden performance.

2 Drawing Sheets

Botanical designation: *Hydrangea paniculata.*
Cultivar denomination: 'LC NO9'.

CROSS-REFERENCED TO CLOSELY RELATED APPLICATIONS

Title: Varieties of *Hydrangea* Plants
Inventor/Applicant: Alex Frederick Schoemaker
Provisional application Ser. No.: 62/973,658
Filed: Oct. 17, 2019
Inventor/Applicant hereby claim the benefit of this provisional U.S. Patent Application.

STATEMENT REGARDING PRIOR DISCLOSURES BY INVENTOR/APPLICANT

An European Community Plant Breeder's Rights application for the instant plant was filed by the Inventor/Assignee, Mr. Alex Frederick Schoemaker of Boskoop, The Netherlands on Oct. 19, 2018, application number 2018/2637. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea paniculata*, commercially referred to as a Hardy or Panicled *Hydrangea* and hereinafter referred to by the name 'LC NO9'.

The new *Hydrangea* plant is a product of a planned breeding program conducted by the Inventor in Boskoop, The Netherlands. The objective of the breeding program is to create new *Hydrangea* plants with uniform plant habit and attractive inflorescences.

The new *Hydrangea* plant originated from a cross-pollination made by the Inventor in July, 2013 in Boskoop, The Netherlands, of *Hydrangea paniculata* 'DVP Pinky', disclosed in U.S. Plant Pat. No. 16,166, as the female, or seed, parent with *Hydrangea paniculata* 'Dharuma', not patented, as the male, or pollen, parent. The new *Hydrangea* plant was discovered and selected by the Inventor as a single flowering plant from within the progeny of the stated cross-pollination in a controlled greenhouse environment in Boskoop, The Netherlands during the summer of 2016.

Asexual reproduction of the new *Hydrangea* plant by vegetative tip cuttings in a controlled environment in Boskoop, The Netherlands since the summer of 2017 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LC NO9'. These characteristics in combination distinguish 'LC NO9' as a new and distinct *Hydrangea* plant:

1. Upright to somewhat outwardly spreading plant habit.
2. Freely branching habit with strong lateral branches.
3. Early and freely flowering habit with plants remaining in flower for a long period time.
4. Dense and hardy inflorescences with large white-colored sterile and prominent white-colored fertile flowers.
5. Good garden performance.

Plants of the new *Hydrangea* can be compared to plants of the female parent, 'DVP Pinky'. Plants of the new *Hydrangea* differ primarily from plants of 'DVP Pinky' in the following characteristics:

1. Inflorescences of plants of the new *Hydrangea* have prominent fertile flowers whereas inflorescences of plants of 'DVP Pinky' have inconspicuous fertile flowers.
2. Sterile flowers of plants of the new *Hydrangea* become more intense dark red in color with development than sterile flowers of plants of 'DVP Pinky'.

Plants of the new *Hydrangea* can be compared to plants of the male parent, 'Dharuma'. Plants of the new *Hydrangea* differ primarily from plants of 'Dharuma' in the following characteristics:

1. Plants of the new *Hydrangea* have glossier leaves than plants of 'Dharuma'.
2. Plants of the new *Hydrangea* have longer inflorescences than plants of 'Dharuma'.
3. Sterile flowers of plants of the new *Hydrangea* become more intense dark red in color with development than sterile flowers of plants of 'Dharuma'.

Plants of the new *Hydrangea* can be compared to plants of the *Hydrangea paniculata* 'Kyushu', not patented. In side-by-side comparisons, plants of the new *Hydrangea* differ primarily from plants of 'Kyushu' in the following characteristics:

1. Plants of the new *Hydrangea* are more compact than plants of 'Kyushu'.
2. Sterile flowers of plants of the new *Hydrangea* become more intense dark red in color with development than sterile flowers of plants of 'Kyushu'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'LC NO9' grown in a container.

The photographs on the second sheet are close-up views of a typical inflorescence (top of sheet) and typical leaves (bottom of sheet) of 'LC NO9'.

DETAILED BOTANICAL DESCRIPTION

Plants used in the aforementioned photographs and in the following description were grown during the late summer in 27-cm containers in an outdoor nursery in Boskoop, The Netherlands and under cultural practices typical of commercial *Hydrangea* production. During the production of the plants, day temperatures ranged from about 16° C. to 35° C. and night temperatures ranged from about 12° C. to 22° C. Plants of the new *Hydrangea* were pinched one time and were two years old when the photographs and description were taken. As a Hardy or Panicled *Hydrangea*, plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea paniculata* 'LC NO9'.

Parentage:

*Female, or seed, parent.*—*Hydrangea paniculata* 'DVP Pinky', disclosed in U.S. Plant Pat. No. 16,166.

*Male, or pollen, parent.*—*Hydrangea paniculata* 'Dharuma', not patented.

Propagation:

*Type cutting.*—By vegetative tip cuttings.

*Time to initiate roots, summer.*—About 16 days at temperatures about 16° C. to 30° C.

*Time to produce a rooted young plant, summer.*—About 120 days at temperatures about 16° C. to 30° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright to somewhat outwardly spreading and uniform plant habit; overall plant shape, broadly upright, obovate to roughly globular; strong and sturdy stems; moderately vigorous growth habit and low growth rate.

*Plant height.*—About 51.8 cm.

*Plant diameter or area of spread.*—About 55.8 cm.

Lateral branch description:

*Branching habit.*—About ten lateral branches develop per plant; pinching enhances lateral branch development.

*Length.*—About 29.1 cm.

*Diameter.*—About 8 mm.

*Internode length.*—About 7 cm.

*Texture.*—When developing, smooth and glabrous; fully developed, woody.

*Aspect.*—Upright to about 20° from vertical.

*Strength.*—Strong, sturdy.

*Color.*—When developing: Close to between 53B and 60A. Developed: Close to between 53A and 59B; proximally, close to 166C; when woody, close to N199A and 200B to 200C.

*Lenticels.*—Density: Moderate; none observed on developing stems. Size, developed stems: About 2 mm by 0.5 mm. Color, developed stems: Close to 54A; with development, becoming closer to 174D.

Leaf description:

*Arrangement*.—Opposite or in whorls of three, simple.

*Length*.—About 12.5 cm.

*Width*.—About 7.7 cm.

*Shape*.—Ovate.

*Apex*.—Apiculate.

*Base*.—Obtuse to truncate.

*Margin*.—Serrate.

*Texture, upper surface*.—Sparsely pubescent; moderately rugose.

*Texture, lower surface*.—Moderately pubescent; moderately rugose.

*Venation pattern*.—Pinnate.

*Color*.—Developing leaves, upper surface: Close to 144A to 144B. Developing leaves, lower surface: Close to between 144B and 146D. Fully developed leaves, upper surface: Close to NN137B slightly tinged with close to 147A; venation, close to 178C, proximally, close to 185A. Fully developed leaves, lower surface: Close to between 146B and 147B; venation, close to N170D, proximally, close to 183C.

*Petioles*.—Length: About 2.4 cm. Diameter: About 3.5 mm. Texture and luster, upper surface: Mostly smooth and glabrous, margins are moderately pubescent; moderately glossy. Texture and luster, lower surface: Sparsely pubescent; matte. Color, upper surface: Close to 183B. Color, lower surface: Close to between 59A and 187C.

Flower description:

*Flower type and habit*.—Showy sterile flowers and prominent fertile flowers arranged on terminal panicles; panicles broadly conical in shape; sterile flowers face mostly upright; fertile flowers face upright to outwardly depending on position on the inflorescence.

*Fragrance*.—Faintly fragrant; sweet to somewhat moldy.

*Natural flowering season*.—Early flowering, flowering begins in the early summer and is continuous until midsummer in Northern Europe.

*Flower longevity*.—Sterile flowers last about five weeks on the plant, sterile flowers persistent; fertile flowers last about five days on the plant, fertile flowers not persistent.

*Quantity of flowers*.—Freely flowering habit; about 17 sterile flowers and about 950 fertile flowers per panicle.

*Panicle height*.—About 13 cm.

*Panicle diameter*.—About 14.1 cm.

*Sterile flower buds*.—Length: About 1 cm. Diameter: About 1.3 cm. Shape: Cup-shaped. Color: Close to 154D; distally, close to 150D.

*Fertile flower buds*.—Length: About 4 mm. Diameter: About 5 mm. Shape: Flattened globular. Color: Close to between 155C and 157D; distally, slightly tinged with close to 59D.

*Sterile flower diameter*.—About 4.3 cm.

*Sterile flower depth* (*height*).—About 1.2 cm.

*Fertile flower diameter*.—About 1.1 cm.

*Fertile flower depth* (*height*).—About 8 mm.

*Petals, sterile flowers*.—Quantity and arrangement: Four arranged in a single whorl. Length: About 4 mm. Width: About 3.5 mm. Shape: Broadly ovate, concave. Apex: Broadly acute. Base: Broadly cuneate. Margin: Entire. Texture and luster, upper surface: Smooth, glabrous; slightly glossy. Texture and luster, lower surface: Smooth, glabrous; matte. Color: When opening, upper surface: Close to between 150D and 155A; towards the margins, close to 155A. When opening, lower surface: Close to 155C; towards the apex, slightly tinged with close to 59D. Fully opened, upper surface: Close to 155A; color does not change with development. Fully opened, lower surface: Close to 155C; color does not change with development.

*Petals, fertile flowers*.—Quantity and arrangement: Five arranged in a single whorl. Length: About 4.5 mm. Width: About 3 mm. Shape: Ovate, concave. Apex: Acute. Base: Broadly cuneate. Margin: Entire. Texture and luster, upper surface: Smooth, glabrous; slightly glossy. Texture and luster, lower surface: Smooth, glabrous; matte. Color: When opening, upper surface: Close to NN155A; towards the margins, close to NN155C. When opening, lower surface: Close to 155C. Fully opened, upper surface: Close to NN155B to NN155C; color does not change with development. Fully opened, lower surface: Close to 155C; color does not change with development.

*Sepals, sterile flowers*.—Quantity and arrangement: Typically four arranged in a single whorl. Length: About 2.2 cm. Width: About 2.2 cm. Shape: Broadly obovate to roughly orbicular. Apex: Obtuse to emarginate. Base: Broadly cuneate. Margin: Entire. Texture and luster, upper and lower surfaces: Smooth, glabrous; matte. Color: When opening, upper surface: Close to 155A. When opening, lower surface: Close to 155B. Fully opened, upper surface: Close to between 155A and 160D; with subsequent development, color becoming closer to 183D. Fully opened, lower surface: Close to 155A; with subsequent development, color becoming closer to 184B with venation, close to 183B.

*Sepals, fertile flowers*.—Quantity and arrangement: Five in a single whorl. Length: About 1 mm. Width: About 2 mm. Shape: Reniform. Apex: Obtuse. Base: Broadly cuneate. Margin: Entire. Texture and luster, upper and lower surfaces: Smooth, glabrous; slightly glossy. Color: When opening and fully opened, upper surface: Close to 157A to 157B; color does not change with development. When opening and fully opened, lower surface: Close to 157A; color does not change with development.

*Pedicels, sterile flowers*.—Length: About 1.9 cm. Diameter: About 1.5 mm. Strength: Moderately strong. Aspect: About 30° from branch axis. Texture and luster: Sparsely to moderately pubescent; matte. Color: Close to between 154D and 157A.

*Pedicels, fertile flowers*.—Length: About 2 cm. Diameter: About 0.5 mm. Strength: Moderately strong. Aspect: About 20° from vertical. Texture and luster: Sparsely to moderately pubescent; matte. Color: Close to 157D.

*Reproductive organs, sterile flowers*.—Stamens: Quantity per flower: About four. Filament length: About 2.5 mm. Filament color: Close to 155C. Anther length: About 1 mm. Anther shape: Broadly oblong. Anther color: Close to 156B. Pollen amount: None observed. Pistils: Pistil quantity per flower: Typically two or occasionally three. Pistil length: About 2 mm. Stigma shape: Club-shaped. Stigma color: Close to 157B. Style length: About 1 mm. Style color: Close to 145C. Ovary color: Close to 145C.

*Reproductive organs, fertile flowers*.—Stamens: Quantity per flower: About eight. Filament length: About 7 mm. Filament color: Close to NN155C. Anther length: About 1 mm. Anther shape: Broadly oblong. Anther color: Close to 161C. Pollen amount: Scarce. Pollen color: Close to 156D. Pistils: Pistil quantity per flower: Typically five or occasionally three or four. Pistil length: About 2 mm. Stigma shape: Club-shaped. Stigma color: Close to NN155A. Style length: About 1 mm. Style color: Close to 160D. Ovary color: Close to 160D.

*Seeds*.—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to be suitable for USDA Hardiness Zones 5 through 9.

It is claimed:

1. A new and distinct *Hydrangea* plant named 'LC NO9' as illustrated and described.

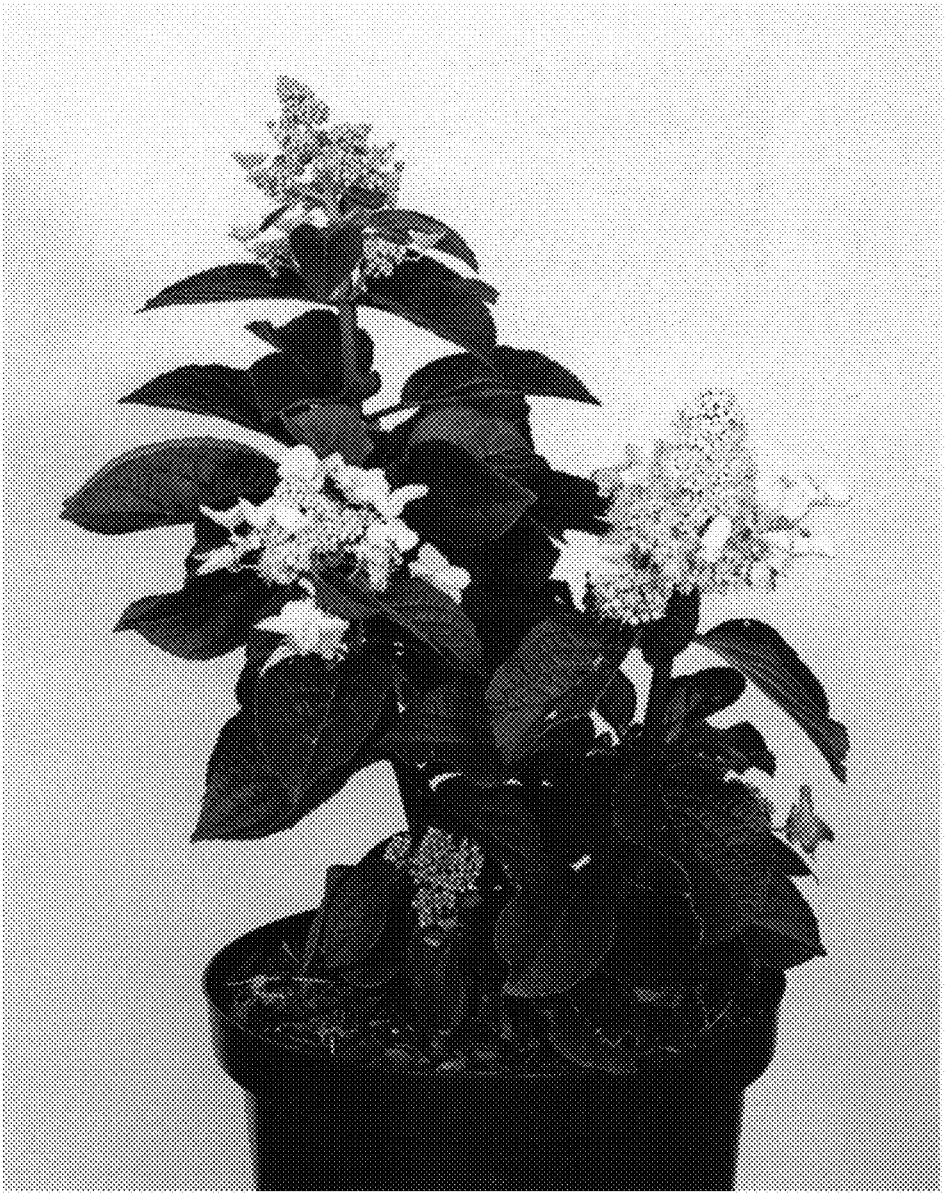

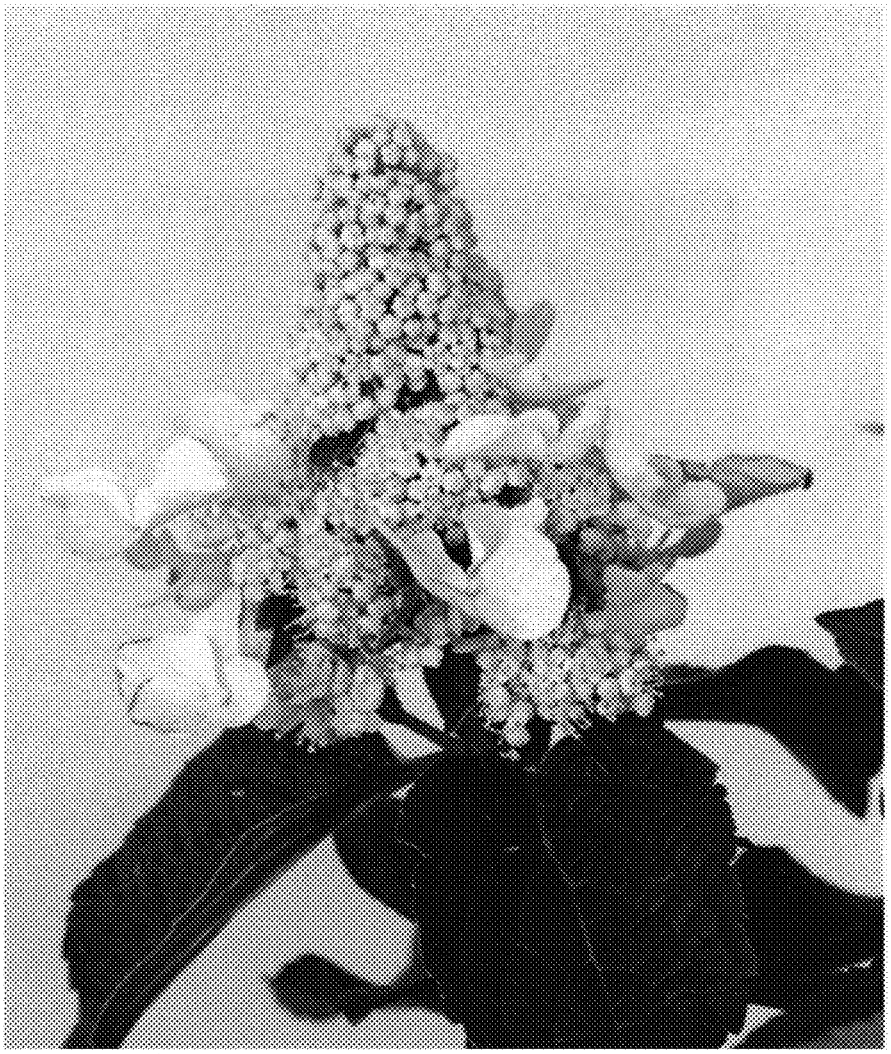
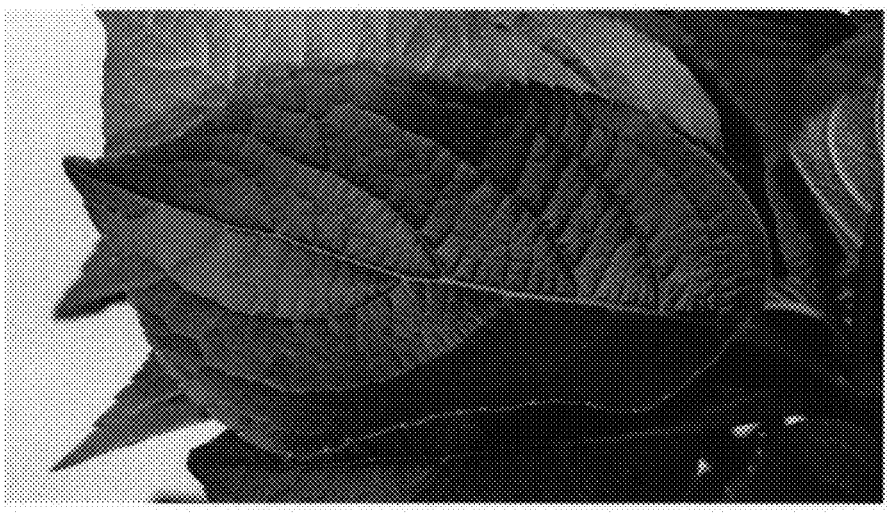

* * * * *